United States Patent [19]

Grossman et al.

[11] Patent Number: 4,979,517
[45] Date of Patent: Dec. 25, 1990

[54] DISPOSABLE STIMULATION ELECTRODE WITH LONG SHELF LIFE AND IMPROVED CURRENT DENSITY PROFILE

[75] Inventors: Phillip A. Grossman, Ann Arbor, Mich.; Cindi J. Nordness, Bothell, Wash.; Gregory W. Shipp, Seattle, Wash.; Harold L. Springer, Kirkland, Wash.; Hung-Yen Kao, Renton, Wash.

[73] Assignee: Physio-Control Corporation, Redmond, Wash.

[21] Appl. No.: 496,121

[22] Filed: Mar. 19, 1990

Related U.S. Application Data

[63] Continuation of Ser. No. 150,604, Feb. 1, 1988, abandoned.

[51] Int. Cl.⁵ ............................................. A61N 1/04
[52] U.S. Cl. ........................... 128/798; 128/802
[58] Field of Search ........ 128/798, 802, 803, 639–641

[56] References Cited

U.S. PATENT DOCUMENTS

| | | | |
|---|---|---|---|
| 3,998,215 | 12/1976 | Anderson et al. | 128/2.06 |
| 4,554,924 | 11/1985 | Engel | 128/640 |
| 4,580,339 | 4/1986 | Toffe | 29/825 |
| 4,674,512 | 6/1987 | Rolf | 128/640 |
| 4,736,752 | 4/1988 | Munck et al. | 128/798 |

FOREIGN PATENT DOCUMENTS

| | | | |
|---|---|---|---|
| 1144606 | 4/1983 | Canada | 128/641 |
| 86/05083 | 9/1986 | World Int. Prop. O. | 128/641 |

OTHER PUBLICATIONS

Williams, C. R. et al., Analysis of the Current–Density Distribution from a Tapered, Gelled–Pad External Cardiac Pacing Electrode, *Medical Instrumentation*, vol. 21, No. 6, Dec., 1987, pp. 329–334.

*Primary Examiner*—Lee S. Cohen
*Attorney, Agent, or Firm*—Christensen, O'Connor, Johnson & Kindness

[57] ABSTRACT

A flexible, disposable stimulation electrode (10) having low current densities and a long shelf life is disclosed. The electrode (10) includes a nonconducting backing layer (12). A tinfoil plate (16) is displaced inwardly from the edge of the backing layer (12), in contact with a skin-facing surface of the backing layer (12). A conductive gel (18) covers the exposed surface of the plate of the plate (16) and a portion of the skin-facing surface of the backing layer (12) that surrounds the plate (16). The gel (18) is formed by a mixture comprising: an ultraviolet radiation (UV) curable resin; a magnesium bromide electrolyte; and, a thioglycerol chain transfer agent. The resin is a urethane-acrylic oligomer made UV curable by the addition of a water-miscible photoinitiator. The gel (18) has an annular tapered edge (52) extending outwardly from the plate (16). The electrode (10) is adhered to a patient's skin by a hypoallergenic adhesive (32) that covers the entire skin-facing surface of the backing layer 12, including the skin-contacting surface (56) of the backing layer (12) that surrounds the gel (18); and, by the surface tack of the gel (18). An electrode post (42), connected to a radially extended arm (48) of the plate (16) and, extending through the backing layer (12), is used to connect the plate (16) to a medical electrode lead. A protective liner (54) is releasably attached to a skin-facing side of the electrode (10).

15 Claims, 2 Drawing Sheets

4,979,517

DISPOSABLE STIMULATION ELECTRODE WITH LONG SHELF LIFE AND IMPROVED CURRENT DENSITY PROFILE

This application is a continuation application based on prior copending application Ser. No. 150,604, filed on Feb. 1, 1988, now abandoned.

FIELD OF THE INVENTION

This invention is directed to electrodes, and more particularly, to disposable medical electrodes.

BACKGROUND OF THE INVENTION

Medical electrodes are used to connect medical electronic equipment, such as medical stimulation equipment, to patients. Stimulation electrodes are affixed to a patient's skin and connected by an electrode lead to an appropriate piece of medical equipment. Electric current generated by the medical equipment is applied to the patient via the electrode. In order to better understand the problems presented by the prior art, and solved by the present invention, a brief discussion of the technological progression of recent years from reusable electrodes to disposable electrodes is presented.

Typically, reusable electrodes were used in conjunction with a separately applied wet gel or paste. The wet gel offered improved adhesive and conductive properties at the point of contact between the electrode and the patient's skin. After the electrode was removed from the patient, both the electrode and the patient's skin had to be cleaned of any gel residue. The reusable electrode was then ready for use with the next patient, after which, the above cleaning process was repeated. Thus, sanitation of the electrodes, personal hygiene, and the mess of the wet gels were problems associated with the reusable electrodes.

The disposable stimulation electrodes used in the prior art were developed to overcome the aforementioned problems. The benefit of such disposable electrodes was that they could be discarded after the first use. Thus, the concerns of sanitation and personal hygiene that existed with reusable electrodes were reduced by using the disposable electrodes. However, many of the disposable electrodes continued to use the wet gels described above. Thus, the mess associated with the wet gels persisted. Eventually, the wet conductive gels that were used with the reusable electrodes gave way to dry conductive gels that formed a part of the disposable electrodes. Typically, the dry gels of the prior art electrodes were not as messy as the wet gels and, therefore, were more convenient to use. However, the dry gels have presented their own problems such as: short shelf life; poor adhesion properties; lack of flexibility; and, patient discomfort during periods of prolonged wear. These problems are discussed in more detail below.

Previous attempts to develop disposable electrodes using dry conductive gels have typically resulted in electrodes that are either too rigid to readily conform to the body contours or have low surface tack properties. As a result, such electrodes tend to fall off patients during periods of extended wear. Another problem associated with disposable electrodes has been their limited shelf life. Corrosion between the electrode plate and the electrolyte used in the dry gel has limited the typical shelf life of disposable electrodes to between six months and one year.

Yet another problem is the nonuniform current density profile associated with the prior art disposable electrodes. Typically, the electric current at the edge of the conductive gel is substantially greater than the electric current near the center of the conductive gel. This unequal current distribution within the gel causes the gel to have a high current density near the edge of the gel. During prolonged periods of repeated stimulation, the high current density causes general discomfort to the patient and potential burning of the patient's skin near the edge of the gel.

As will be readily appreciated from the foregoing discussion, there is a need for a disposable electrode that: remains adhered to the patient's skin for extended periods of time; has a long shelf life; is convenient to use; and offers improved current density thereby reducing patient discomfort and burning during prolonged periods of repeated stimulation. Additionally, such an electrode should be easily and inexpensively manufacturable.

SUMMARY OF THE INVENTION

In accordance with the present invention, a flexible, disposable stimulation electrode that has an improved current density profile and is corrosion resistant is provided. The disposable electrode comprises a flexible metal plate, preferably a tinfoil plate, located on one surface of a flexible nonconductive backing layer and coated with a conductive gel. The outer edge of the metal plate is located inwardly of the outer edge of the backing layer. An electrode post, connected to the plate, conducts electric current from a piece of medical equipment to the plate. The conductive gel, which has a low resistivity, includes an ultraviolet radiation (UV) curable resin that functions as a gel matrix for holding other constituents of the gel. The resin is made conductive by adding an electrolyte, preferably magnesium bromide. The adhesive properties of the gel are improved by adding a sulfur-based, chain transfer agent to the gel prior to the UV curing process. The chain transfer agent is preferably thioglycerol.

In further accordance with the present invention, the conductive gel has a tapered portion extending outwardly from the outer edge of the metal plate to the outer edge of the gel. As a result, the skin-contacting surface area of the gel is larger than the surface area of the gel that is in contact with the metal plate. The tapered edge of the gel reduces the flow of electric current to the edge of the gel. The reduced current flow to the edge results in an improved current density profile. Thus the tapered edge of the gel produces a stimulation electrode that has an improved patient comfort level and a reduced likelihood of burning the patient's skin.

In still further accordance with the invention, the backing layer is larger than the skin-contacting surface of the gel. Thus the skin-facing side of the backing layer includes an outer annular portion surrounding the skin-contacting surface of the gel. The outer annular portion of the backing layer is coated with a hypoallergenic adhesive. The electrode is held in place on the patient's skin by the aforementioned adhesive on the outer annular portion of the backing layer and by the improved surface tack of the conductive gel. The skin-facing side of the electrode is covered by a protective liner that is removed prior to applying the electrode to a patient's skin.

BRIEF DESCRIPTION OF THE DRAWINGS

The foregoing and other features and advantages of this invention will become more readily appreciated as the same becomes better understood by reference to the following detailed description, and when taken in conjunction with the accompanying drawings, wherein.

DESCRIPTION OF THE PREFERRED EMBODIMENT

As is well known in the medical electrode art, there is a need to provide a disposable stimulation electrode that will adhere to a patient's skin during periods of extended wear and remain relatively comfortable to the patient during periods of prolonged repeated stimulation. Furthermore, the electrode should have a long shelf life. The present invention provides a disposable stimulation electrode having these features and more.

Figure 1:
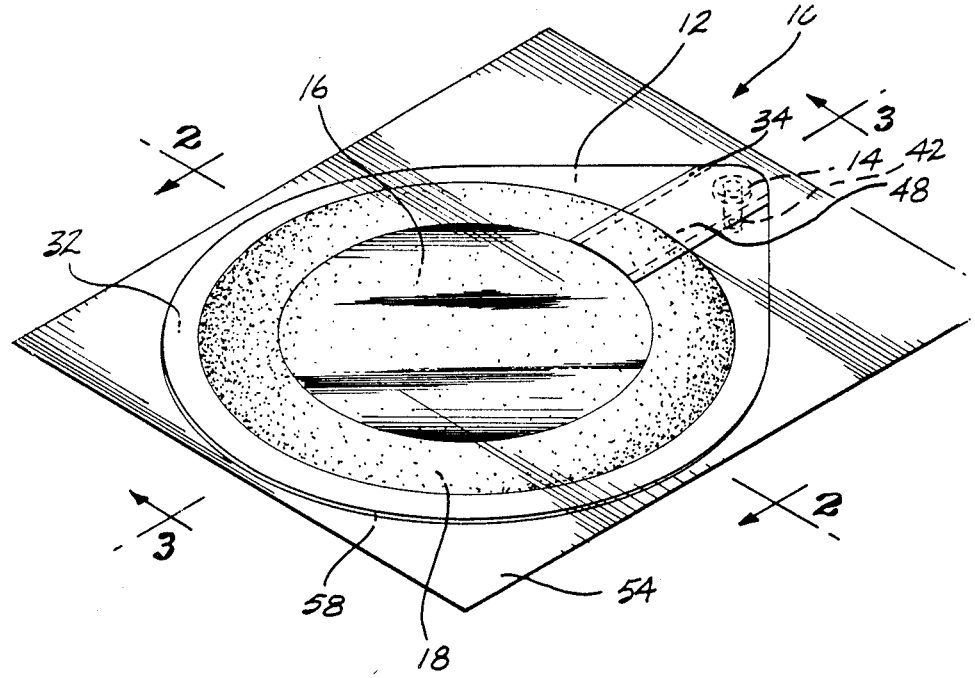
FIG. 1 is a isometric view of an apparatus formed in accordance with the invention.
Figure 2:
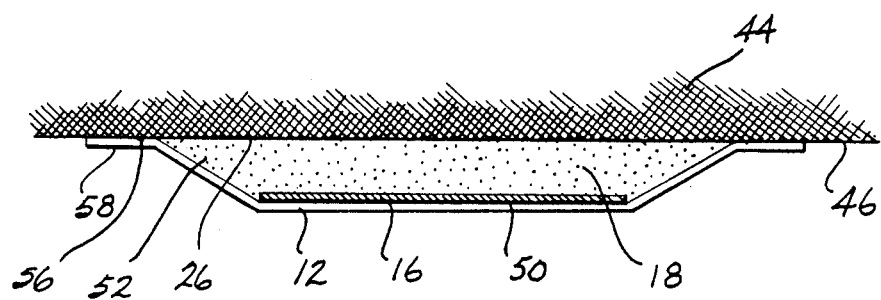
FIG. 2 is a sectional view along lines 2—2 of FIG. 1 that is exaggerated in the vertical direction so that certain features of the invention can be more clearly viewed.

FIG. 1 illustrates an electrode 10 formed in accordance with the invention comprising: a nonconductive backing layer 12; a layer of conductive gel 18; a thin, circular metal plate 16 having a radially extended arm 48; an electrode post assembly 14 including an electrode post 42; insulating tape 34; and, a protective liner 54. The electrode post 42 is further disclosed in U.S. Pat. No. 4,671,591. The metal plate 16 and the conductive gel 18 are generally concentric with each other and are bonded to one surface of the nonconductive backing layer 12. The nonconductive backing layer 12 is preferably formed of a flexible, nonwettable material having a high dielectric characteristic. A suitable material is polyethylene. The protective liner 54 is releasably attached to the electrode 10. More specifically, the protective liner overlies the conductive gel 18 and an outer annular portion 58 of the backing layer 12 and protects these elements from external contaminants. As illustrated in FIG. 2, the protective liner 54 is removed prior to placing the electrode 10 on a patient's body 44. Preferably, the protective liner 54 is transparent, allowing the electrode 10 to be visibly inspected prior to use.

As illustrated in FIG. 2, and as will be discussed in greater detail below, a skin-contacting surface 26 of the conductive gel 18 is larger than the metal plate 16. Further, the backing layer 12 is larger than the skin-contacting surface 26 of the conductive gel 18. As a result, the outer annular portion 58 of the backing layer 12 extends beyond the gel 18. As will be discussed in greater detail below, a hypoallergenic adhesive 32 (illustrated in FIG. 4) is applied to a skin-facing surface of the backing layer 12 to facilitate adherence of the metal plate 16 to the backing layer 12 and to facilitate the adherence of the electrode 10 to the patient's skin 46.

Figure 3:
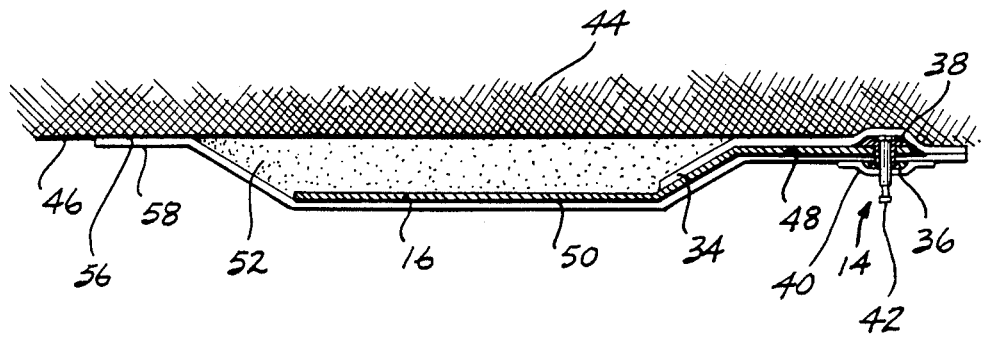
FIG. 3 is a sectional view along line 3—3 of FIG. 1 that is exaggerated in the vertical direction so that certain features of the invention can be more clearly viewed.

FIG. 3 illustrates how the electrode post assembly 14 is electrically connected to metal plate 16. The electrode post assembly 14 comprises: the electrode post 42; and, a clothing snap fastener consisting of a female snap end 36 and a male snap end 38. The electrode post 42 extends through the backing layer 12 and the radially extended arm 48 of the metal plate 16. The post 42 is affixed by means of the standard clothing snap fastener. More specifically, the female snap end 36 of the clothing snap fastener is positioned on the electrode post 42, in contact with the top, or nonskin-facing side, of the backing layer 12. The male snap end 38 of the snap fastener is positioned to engage the electrode post 42 and the arm 48 of the metal plate 16 from the skin-facing side of the electrode 10. The male snap end 38 is connected to the female snap end 36 in a conventional clothing snap manner, as shown in FIG. 3, by crimping the leg of the male snap end 38 that passes through the hole in the female snap end 36. An adhesive, insulated back ring 40 covers the female snap end 36. The electrode post 42 extends through the insulated back ring 40.

Figure 4:
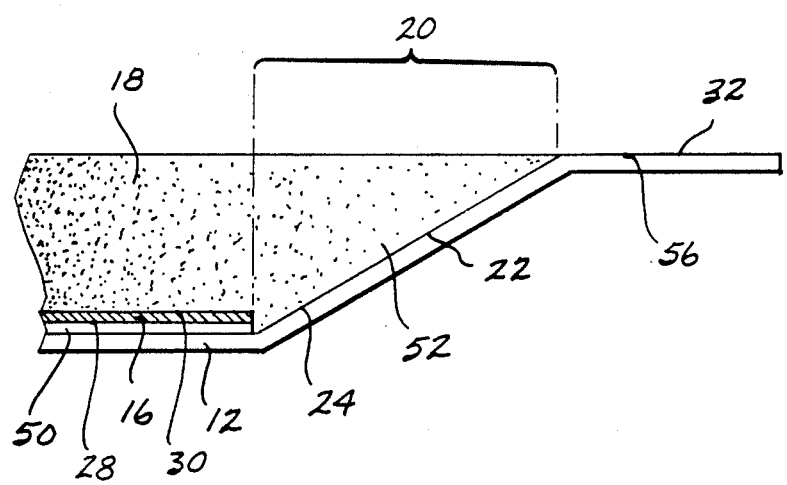
FIG. 4 is an enlarged sectional view of a portion of the apparatus illustrated in FIG. 1 that is also exaggerated in the vertical direction to permit the clearer viewing of certain features of the invention.

FIG. 4 illustrates that one surface 28 of the metal plate 16 is in intimate contact with a support sheet 50 that will be discussed in greater detail below. The support sheet 50 is in intimate contact with a portion of the skin-facing surface of the backing layer 12. A nonskin-contacting surface 24 of the gel 18 is in intimate contact with another surface 30 of the metal plate 16 and with the portion of the skin-facing surface of the backing layer 12 that surrounds the metal plate 16. As illustrated in FIG. 3, the radially extended arm 48 of the metal plate 16 is in initimate contact with the support sheet 50. The support sheet 50 is in intimate contact with the skin-facing surface of the backing layer 12. The double-sided, adhesive insulating tape 34 covers the skin-facing side of the radially extended arm 48. The insulating tape 34 also covers the male snap end 38 of the clothing snap fastener.

In accordance with the embodiment of this invention, the metal plate 16 and the arm 48 of the metal plate 16 are made from tinfoil. The tinfoil, preferably, is 99.98% tin and 2-mils thick. While the purity and thinness of the tinfoil makes the plate 16 and the arm 48 very flexible, it also makes them susceptible to damage during manufacturing of the electrode 10. In order to increase the durability of these elements during manufacturing, as illustrated in FIG. 4, preferably, a support sheet 50 (preferably, 1-mil polypropylene) is adhesively laminated to the nonskin-contacting surface 28 of the metal plate 16 and the arm 48.

Turning next to a description of a preferred composition of the conductive gel 18, the gel 18 comprises: a gel matrix; an electrolyte; and, a chain transfer agent. The gel matrix includes a water-reducible, urethane-acrylic oligomer resin such as the Polymer Systems Corporation, 16 Edgeboro Road, East Brunswick, N.J. 08816, Product No. PL 153A. The oligomer resin is cured (i.e., polymerized) by exposure to ultraviolet radiation (UV). A water-miscible photoinitiator is added to the oligomer resin to act as a catalyst for the UV curing process. A suitable photoinitiator is "DAROCUR 1173," produced by E M Industries, 5 Skyline Drive, Hawthorne, N.Y. 10532. The electrolyte is magnesium bromide ($MgBr_2$) and the chain transfer agent is a sulfur compound, preferably thioglycerol ($C_3H_8O_2S$). The metal plate 16 and the electrolyte combine to form a metal/metal salt combination (i.e., tin/magnesium bromide) that is less corrosive than the metal/metal salt combinations used in the prior art. The noncorrosive property of the tin/magnesium bromide combination gives the electrode 10 a useful shelf life of two years or more.

In accordance with the preferred embodiment of the invention, Table A below lists each constituent of the conductive gel 18 as a percentage of the total gel composition, prior to curing.

TABLE A

| Compound (Function) | Percentage of Total Composition (By Weight) |
|---|---|
| PL 153A (Gel Matrix Resin) | 48% |
| Water (Mixing Agent) | 45% |
| Magnesium Bromide (Electrolyte) | 5% |
| Thioglycerol (Chain Transfer Agent) | 1.12% |
| Methylparaben (Preservative) | .04% |
| DAROCUR 1173 (Photoinitiator) | .84% |

A preferred method for making the gel 18 is to mix the constituents set forth in Table A, and permit the constituents to react to produce an uncured gel solution. Backing layer 12 is placed atop a suitable mold with the skin-facing surface up, and the hypoallergenic adhesive 32 is applied to the skin-facing surface of the backing layer 12. Alternatively, the hypoallergenic adhesive 32 may be applied to the backing layer 12 prior to placing the backing layer on the mold. Next, the metal plate 16, including the arm 48, is placed on the backing layer 12 with the support sheet 50 in contact with the backing layer 12. As was stated above, the edge of the metal plate 16 is located inwardly of the edge of the backing layer 12, on the skin-facing surface of the backing layer 12. The arm 48 extends radially from the metal plate 16 towards, but not beyond, an outside edge of the backing layer 12. A crimping machine secures the electrode post assembly 14 to the backing layer 12 and the arm 48 in the manner described above. The adhesive insulating tape 34 is then applied in the manner also described above. The tape 34 electrically insulates the arm 48 of the metal plate 16 and the electrode post assembly 14 from direct contact with the patient's body 44.

Once the above steps are completed, a vacuum is applied to a central portion of the electrode 10, to form a reservoir having inwardly sloping sides. The uncured gel solution is then poured into the reservoir and cured. The thioglycerol controls the amount of the cross-linking and results in a cured gel having a high tack and improved elongation and memory characteristics. The protective liner 54 is then applied to the skin-contacting side of the electrode 10 and the electrode 10 is packaged for customer use.

The inwardly tapering sides of the reservoir cause the edge 52 of the gel 18 to be tapered. The tapered edge 52 is illustrated best in FIG. 4 and includes a setback 20 and a slant 22. The slant 22 lies between the outside edge of the metal plate 16 and the inside edge of the skin-contacting surface 56 of the backing layer 12. As will be discussed in more detail below, the tapered edge 52 reduces the amount of electric current at the edge of the gel 18, thereby improving the current density profile of the electrode 10.

Electrodes in the prior art typically do not have a gel layer that is tapered at the outer edges. Instead, the gel layer of the prior art disposable electrodes has an edge that is generally normal (i.e., perpendicular) to the skin-contacting surface of the gel layer. Such a gel edge has a higher than desirable current density at the edge of the skin-contacting surface 26 of the gel layer 18 (the so-called "edge effect") due to the resistivity of the gel being low. After periods of prolonged repeated stimulation, the high edge current density of the prior art electrodes may cause general discomfort and burning of the patient's skin at the edges of the gel layer. As next described, this edge effect is overcome by tapering the edge of the gel because gel impedance increases as gel thickness decreases and because current flow to the edge of the skin-contacting surface 26 of the gel layer 18 decreases as impedance increases, with an associated decrease in edge current density.

It is a well-known electrical principle that, when given a choice, electric current will follow the path of least resistance. Thus, current flow through a body having varying cross-sectional impedance will vary from region to region. In the case of the electrode of the present invention, the increasingly higher impedance of the tapered edge 52 of the gel 18 causes the electric current, flowing through the gel 18, to move away from the edge of the gel 18, towards the center of the gel 18. Since less current flows to the edge of the gel 18, the current density at the edge of the gel 18 is reduced. Contrariwise, the current density towards the center of the gel 18 increases. The resulting lower current density at the edge and increased current density towards the center of the gel 18 improves the current density profile of the electrode 10. More specifically, the current density profile is improved because the lower current density at the edge of the gel 18 reduces the patient discomfort and burning that is prevalent with prior art electrodes.

The dimension of the setback 20 (FIG. 4) is determined by the particular use of the electrode 10. When patient comfort is of primary concern, the setback 20 is typically larger than when patient comfort is outweighed by other factors such as conductive plate area relative to gel surface area or electrode flexibility. For example, patient comfort is very important during noninvasive cardiac pacing. Pacing typically involves a conscious patient who may be attached to the electrodes for extended periods of time and is receiving repeated, low-amplitude stimulation pulses. During this time, a high current density at the edge of the gel 18 may cause patient discomfort and burning. Therefore, pacing electrodes should have a relatively large setback 20 to increase the distance the current must travel from the edge of the plate 16 to the edge of the gel 18. The increased distance results in a higher impedance that reduces the current density near the edge of the electrode 10. In other instances, electrode flexibility, excellent skin contact, and the ability to deliver high current levels efficiently outweigh patient comfort concerns. In such a situation, a smaller setback 20 may be appropriate. An example of the latter situation arises during patient defibrillation. During defibrillation, a patient is unconscious and, therefore, the patient's comfort is of little concern. Also, since high electric current levels are applied during defibrillation (i.e., high, relative to pacing current levels), it is imperative that good electrode-to-skin contact be maintained so that maximum energy is transferred to the patient. In accordance with the invention, the preferred set back of a disposable stimulation electrode 10 used for noninvasive cardiac pacing a patient is ¾", whereas the preferred set back of an electrode 10 used for defibrillating a patient is 3/16". In both electrodes, the thickness of the nontapered portion of the gel 18 is preferably 1/16".

Stimulation electrodes 10 formed in accordance with the preferred embodiment of the invention have a low impedance that makes them ideally suited for use as defibrillation as well as for pacing electrodes. More specifically, the resistivity ($\rho$) of the gel 18 is low, preferably approximately 200$\Omega$-cm. The low resistivity of the gel 18 results in a low electrode impedance—less than 2$\Omega$. The low electrode impedance allows pacing signals, which are relatively small (e.g., 100 ma), to be effectively transmitted to a patient without significant signal loss. Likewise, the low electrode impedance also allows defibrillation of the patient with high current levels (e.g., 10-20 A) without abnormally high amounts of power loss (i.e., $I^2R$ loss) through the electrode. Thus, the stimulation electrode 10 formed in accordance with the present invention is equally suitable for defibrillation and pacing of patients.

Therefore, as can be readily appreciated from the foregoing description, the present invention provides a flexible, disposable stimulation electrode that remains adhered to the patient, while reducing patient discomfort during periods of prolonged repeated stimulation. The invention also has a long shelf life.

While a preferred embodiment of the invention has been disclosed and described, it is to be understood that various changes can be made without departing from the spirit and scope of the invention. For example, another sulfur compound could be substituted for thioglycerol as the chain transfer agent. The thickness of the tinfoil plate can be varied and the electrode post assembly 14 could be mounted in a different location or by other than the conventional clothing snap arrangement described above. Likewise, the dimensions of the setback 20 and thickness of the gel 18 can vary. In other words, within the scope of the appended claims, the invention can be practiced otherwise than as specifically described herein.

The embodiments of the invention in which an exclusive property or privilege is claimed are defined as follows:

1. A disposable stimulation electrode suitable for placing in contact with a patient's skin to conduct electric current from a medical device to the patient, comprising:
   (a) a flexible backing layer having a skin-facing surface, a back surface and an edge;
   (b) a receiving means for receiving electric current from a medical device, said receiving means comprising a flexible tin plate, said tin plate mounted on said skin-facing surface of said backing layer inwardly of said edge of said backing layer; and,
   (c) a conductive gel layer overlying said flexible tin plate, said conductive gel layer comprising a magnesium bromide electrolyte.

2. The disposable stimulation electrode claimed in claim 1, wherein said conductive gel layer further comprises: a chain transfer agent for increasing the surface tack of said conductive gel layer.

3. The disposable stimulation electrode claimed in claim 2, wherein said chain transfer agent comprises a sulfur-containing compound.

4. The disposable stimulation electrode claimed in claim 3, wherein said sulfur-containing chain transfer agent is thioglycerol.

5. A disposable stimulation electrode suitable for placing in contact with a patient's skin to conduct electric current from a medical device to the patient, comprising:
   (a) a flexible backing layer having a skin-facing surface, a back surface and an edge;
   (b) a receiving means for receiving electric current from a medical device, said receiving means including a flexible metal plate mounted on said skin-facing surface of said backing layer inwardly of said edge of said backing layer; and,
   (c) a conductive gel layer overlying said flexible metal plate, said conductive gel layer formed by ultraviolet radiation curing a mixture comprising a sulfur-containing chain transfer agent for increasing the surface tack of said conductive gel layer.

6. The disposable stimulation electrode claimed in claim 5, wherein said sulfur-containing chain transfer agent is thioglycerol.

7. The disposable stimulation electrode claimed in claim 5, wherein said ultraviolet radiation-curable mixture further comprises:
   (a) a urethane-acrylic oligomer; and,
   (b) a water-miscible photoinitiator that causes polymerization of said urethane-acrylic oligomer when exposed to ultraviolet radiation.

8. The disposable stimulation electrode claimed in claim 7, wherein said sulfur-containing chain transfer agent is thioglycerol.

9. The disposable stimulation electrode claimed in claim 5, wherein said electrode further comprises adhesive means for adhering said electrode to a patient's skin, said adhesive means comprising a hypoallergenic adhesive on a skin-contacting portion of said skin-facing surface of said backing layer.

10. A disposable stimulation electrode suitable for placing in contact with a patient's skin to conduct electric current from a medical device to the patient, comprising:
    (a) a flexible backing layer having a skin-facing surface, a back surface and an edge;
    (b) a receiving means for receiving electric current from a medical device, said receiving means including a flexible metal plate mounted on said skin-facing surface of said backing layer inwardly of said edge of said backing layer; and,
    (c) a conductive gel layer overlying said flexible metal plate, said conductive gel layer comprising a means for reducing current density about the periphery of said conductive gel layer.

11. The disposable stimulation electrode claimed in claim 10, wherein said means for reducing current density about the periphery of said conductive gel layer comprises a tapered portion of said conductive gel layer that begins at an outer edge of said flexible metal plate and tapers outwardly to an outer edge of said gel layer.

12. The disposable stimulation electrode claimed in claim 11, wherein said conductive gel layer is formed from a mixture comprising:
    (a) a magnesium bromide electrolyte;
    (b) an ultraviolet radiation-curable resin; and,
    (c) a sulfur-containing chain transfer agent for increasing the surface tack of said gel layer.

13. The disposable stimulation electrode claimed in claim 12, wherein said ultraviolet radiation-curable resin comprises:
    (a) a urethane-acrylic oligomer; and,
    (b) a water-miscible photoinitiator that causes polymerization of said urethane-acrylic oligomer when exposed to ultraviolet radiation.

14. The disposable stimulation electrode claimed in claim 13, wherein said sulfur-containing chain transfer agent is thioglycerol.

15. The disposable stimulation electrode claimed in claim 12, wherein said electrode further comprises adhesive means for adhering said electrode to a patient's skin, said adhesive means comprising a hypoallergenic adhesive on a skin-contacting portion of said skin-facing surface of said backing layer.

* * * * *